United States Patent

Likhosherstov et al.

[11] 4,083,976
[45] Apr. 11, 1978

[54] 10'-(ω-N)-1,4-DIAZABICYCLO(4,3,0)-ALKANYL-LACYL) -PHENOTHIAZINE COMPOSITIONS

[76] Inventors: Arkady Mikhailovich Likhosherstov, Smolnaya ulitsa, 33, kv. 107; Liya Semenovna Nazarova, Petrovsko-Razumovsky proezd, 20, kv. 22; Alexandr Petrovich Skoldinov, ulitsa Alabyana, 3, korpus 1, kv. 60; Galina Alexandrovna Markova, Kotelnicheskaya naberezhnaya, 1/15, kv. 320; Natalya Veniaminovna Kaverina, Novopeschanaya ulitsa, 3, kv. 32, all of Moscow, U.S.S.R.

[21] Appl. No.: 726,259

[22] Filed: Sep. 24, 1976

Related U.S. Application Data

[60] Division of Ser. No. 485,155, Jul. 1, 1974, Pat. No. 3,998,820, which is a continuation of Ser. No. 230,987, Mar. 1, 1972, abandoned.

[51] Int. Cl.$^2$ ............................................. A61K 31/54
[52] U.S. Cl. .................................................... 424/247
[58] Field of Search ........................................ 424/247

[56] References Cited
U.S. PATENT DOCUMENTS

| | | | |
|---|---|---|---|
| 2,591,679 | 4/1952 | Cusic | 260/243 A |
| 2,694,705 | 11/1954 | Cusic | 260/243 A |
| 3,055,891 | 9/1962 | Cusic | 260/243 A |
| 3,320,246 | 5/1967 | Cusic et al. | 260/243 A |

*Primary Examiner*—Albert T. Meyers
*Assistant Examiner*—Daren M. Stephens
*Attorney, Agent, or Firm*—Haseltine, Lake & Waters

[57] ABSTRACT

Novel compounds 10'-[ω-N/1,4-diazabicyclo(4,m,0)-alkanyl/-acyl] -phenothiazines having the formula:

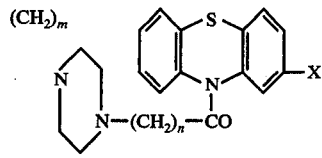

wherein X = H, Cl, CF$_3$; n = 1, 2, 3; m = 3, 5; and their salts of acidic addition and quaternary salts. The process for producing said compounds comprises reacting ω-chloracyl -2-substituted phenothiazines with 1,4-diazabicyclo(4,m,0)-alkanes in an inert solvent medium at a temperature of 50–140° C followed by isolation of the desired product.

Said compounds are pharmacologically active. The most active compound 10'- [β-N-/1,4-diazabicyclo-(4,3,0)-nonanyl/-propyonyl]-2'-chlorophenothiazine of the formula:

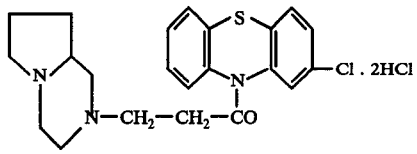

is an active principle of a medicated compound possessing spasmolytic and coronary-dilatant effect.

4 Claims, No Drawings

10'-(ω-N)-1,4-DIAZABICYCLO(4,3,0)-ALKANYL-LACYL)-PHENOTHIAZINE COMPOSITIONS

This is a divisional application of U.S. patent application Ser. Number 485,155, filed July 1, 1974, now U.S. Pat. No. 3,998,820 granted Dec. 21, 1976 which, in turn, is a continuation of U.S. patent application Ser. No. 230,987, filed Mar. 1, 1972, now abandoned.

The present invention relates to a process for producing novel compounds, viz. 10'-(ω-N-/1,4-diazabicyclo/-4,m,0/-alkanyl/-acyl)-phenothiazines, their salts of acidic addition and quaternary salts.

Said compounds correspond to the following general formula:

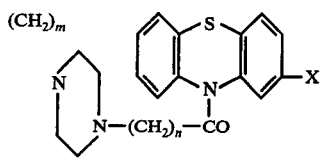

wherein X=H; Cl; $CF_3$; n=1; 2; 3; m= 3; 5.

The compounds according to the present invention and their salts of acidic addition as well as quaternary salts possess pharmacological activity and show spasmolytic and coronary-dilatant properties.

The novel compounds according to the present invention are solids or, in most cases, high-boiling oils.

Salts of said compounds are crystalline powders having white or cream-white color. They are well-soluble in water, aqueous alcohol, but insoluble in ether, chloroform and other organic solvents.

Said compounds possess spasmolytic and coronary-dilatant properties, whereby they have found a wide application in medicine.

The process for producing said compounds, according to the invention, comprises reacting ω-chloracyl-2-substituted phenothiazines with 1,4-diazabicyclo-4(m,0)-alkanes in an inert organic solvent medium at a temperature of 50°–140° C followed by isolation of the desired product.

Said compounds possess spasmolytic and coronary-dilatant action. The most active compound is 10'-(β-N-/1,4-diazabicyclo-(4,3,0)-nonanyl/-propyonyl)-2'-chlorophenothiazin of the formula:

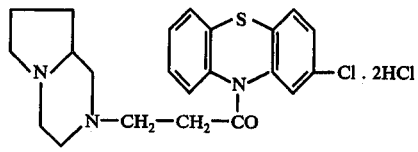

This compound of the present invention is an active principle of a medicated compound possessing coronary-dilatant and spasmolytic action, which compound is referred to hereinafter as nonachlazine.

The medicated compound is employed for cutting short stenocardia attacks as well as for treating seriously ill coronary patients during the exacerbation period. The indication for application of the medicated compound is ischemic heart disease of all the three stages; stenocardia attacks; cardiac muscle infarction.

Pharmacological studies have shown that the medicated compound possesses a pronounced vascular dilatant action, mainly upon the coronal artery system.

Experiments carried out on cats and rats have demonstrated that the medicated compound when intravenously injected at a rate of 5–7 mg./kg considerably improves blood supply of the heart increasing the coronary blood flow by 120% for 30–60 minutes. The level of arterial system pressure is not substantially changed therewith.

Oxygen consumption by the heart is increased in parallel with the growth of coronary blood flow under the influence of the medicated compound. As it has been revealed by further studies relating to registration of coronary vascular resistance by a resistography method, the effect of the medicated compound of the present invention is connected with its direct influence upon coronary vascular tone. Under the influence of the medicated compound a reduction of coronal vascular resistance by 25–35% (average) is observed.

The medicated compound does not result in electrocardiagram changes, neither it noticeably affect the vegetative nervous system and the central nervous system.

The compound is only slightly toxicant and has sufficiently wide range of a therapeutic action. During the study of a sharp toxicity of the medicated compound it has been found that upon intravenous infusion thereof to white mice having 23–26 g. body weight, the $LD_{50}$ is 55 mg./kg.

The medicated compound of the present invention possesses a spasmolytic action eliminating the spasm of intestinal smooth musculature caused by barium chloride.

By its intensiveness of the coronary-dilatant action the medicated compound of the present invention is superior to 2-chloro-10-(β-diethylaminopropyonyl)-phenothiazine chlorohydrate, persantine, papaverine, segoptine, intensaine, and nitroglycerol.

The medicated compounds has been clinically tested in six clinics on 300 patients.

The compound was prescribed at a rate of 30 mg. three times per day to patients with angina pectoris exacerbation and frequent stenocardia attacks relieved only by narcotics; to patients with fresh cardiac muscle infarction accompanied by frequent attacks and pains; to patients with fresh smallseat necrosis; to seriously ill coronary patients during the exacerbation period.

There has been observed a good endurance of the compound by the patients; there have been no side-effects upon the application of the compound. The compound has been well borne by patients with tachycardia and bradycardia, and also with ulcer disease and cholecystitis. No changes of arterial pressure have been observed. Neither there have been observed changes on the part of blood and urine, during the application of the compound. There have been no gastritic complaints. Also there have no been observed electrocardiogram deviations due to the application of the medicated compound. One of the criteria for evaluating the effectiveness of the compound was the amount of nitroglycerol tablets taken daily in the beginning and at the end of the treating. The number of nitroglycerol tablets have been reduced more than twice upon combined application with the compound.

It has been noted that in 104 cases from 108 stenocardiac pains were completely relieved or became weak and rare after taking the medicated compound. In 2 cases there have remained pain attacks which could not be relieved even by nitroglycerol. In 17 cases the treatment have been effected alternately using the compound at a rate of 30 mg. three times per day during four days and placebo at a rate of 0.00 g. three times per day during four days.

Placebo has been employed until the complete disappearance of pains owing to the compound. The results of treatment with placebo after the application of the medicated compound of the present invention are given in the following table.

| Number of | Frequency of stenocardia attacks | | | |
| --- | --- | --- | --- | --- |
| patients | 1th day | 2nd day | 3rd day | 4-th day |
| 5 | — | 1 | 2–3 | 2–3 |
| 6 | — | 2 | 3–4 | 2–3 |
| 6 | 1 | 3 | 3–4 | 4–5 |

When employing placebo pain attacks renewed which proves the absence of an after-action of the compound and its obvious efficiency.

By its efficiency of action and rapidity of the effect manifestation the medicated compound of the present invention is superior to many other remedies used at exacerbation of ischemic heart disease such as papaverine, inderal, intensaine, isoptine, 2-chloro-10-($\beta$-diethylaminopropyonyl)-phenothiazine chlorohydrate, corontine and the like. Indication to the application of this compound is the beginning of an exacerbation period of coronary disease with frequent and lasting pains. Under the influence of the compound of the present invention patients easily overcome a dangerous period of the disease exacerbation. Further, after stable reducing or disappearance of pains it is possible to give the patients other medicines possessing an after-action, i.e. residual effect. It is also possible to use a combined treatment with the compound and 2-chloro-10-($\beta$-diethylaminopropyonyl)-phenothiazine chlorohydrate, nitroglycerol, or intensaine or medicated compounds of the inderal-isoptine group.

The medicated compound of the present invention, freeing patients from difficult-to-cut short and unprophylactized with other means stenocardia attacks, makes it possible to help patients out of an exacerbation period without development of necrosis.

The medicated compound of the present invention may be employed as it is in a powder-like form.

According to the invention, the medicated compound may contain the active principle in combination with a pharmaceutical filler.

As the pharmaceutical filler it is advantageous to employ starch or sugar powder. Therewith, the active principle content of the compound is of 15–90 mg. per one reception.

The compound is employed in the form of tablets weighing 0.3 g.

The treatment course lasts three weeks at a rate of one tablet three times per day. For cutting short stenocardia attacks the treatment is carried out once a week at a rate of one tablet three times per day. Disappearance of pain is observed even on the first or second day after taking the compound.

The compound may be stored without losing its activity in a light-protected place.

The present invention also relates to the process for producing 10'-($\omega$-N-/1,4-diazabicyclo(4,m,0)-alkanyl/-acyl)-phenothiazines, their salts of acidic addition and quaternary salts.

To accelerate the reaction a catalyst such as iodine salts is employed in the process.

The process for producing 10'-($\omega$-N-/1,4-diazabicyclo/-4,m,0/-alkanyl/-acyl)-phenothiazines is effected in accordance with the following scheme:

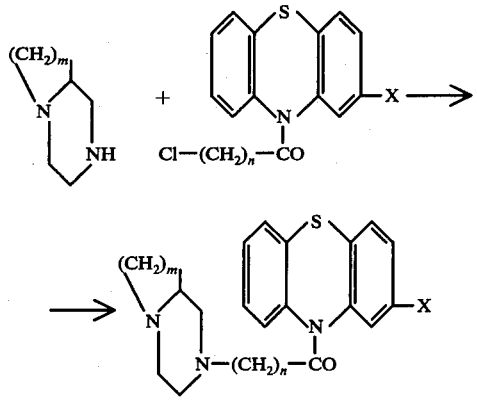

wherein m = 3 or 5 n=1; 2; 3; X = H; Cl; CF$_3$.

The process of condensation of 1,4-diazabicyclo (4,m,0)-alkanes and $\omega$-chloracylphenothiazines is effected in organic solvents which are inactive in respect of the reagents employed (such as benzenes, toluene or xylene), the duration of the process being dependent on temperature conditions and adjusted by choosing an appropriate solvent. The process temperature varies within the range of from 50° to 140° C; the process duration - from 3 to 20 hours.

To increase the yield of the desired product the reaction is carried out in the presence of basic substances, viz. sodium carbonate or triethylamine, for the purposes of binding the evolving hydrogen chloride.

Tertiary nitrogen atoms of the resulting desired product or an excessive amount of 1,4-diazabicyclo(4,m,0)-alkane may serve as an acceptor for hydrogen chloride evolving during the reaction.

Bis-quaternary salts of said compounds are obtained by treating the resulting bases with an excessive amount of a haloalkyl such as methyl iodide. The isolation of acidic addition salts is effected by conventional techniques.

The yield of the desired products is of 40–80% by weight.

For a more complete understanding of the present invention reference will now be made to the following specific examples illustrating the process for producing 10'-($\omega$-N-/1,4-diazabicyclo/4,m,o/-alkanyl/-acetyl-phenothiazines, their salts of acidic addition and quaternary salts.

EXAMPLE 1

To a solution of 7.2 g of 10-($\beta$-chloropropyonyl)-2-trifluoromethylphenothiazine in 70 ml. of anhydrous toluene 5.04 g. of 1,4-diazabicyclo-(4,3,0)-nonane are added and the mixture is boiled for three hours. When the heating is stopped, the toluene solution is washed with water and acidified with a diluted solution of hydrochloric acid. The acidic aqueous solution is boiled with activated carbon for 0.5 hour, filtered and the filtrate is alkalized with a 10% caustic soda solution, whereafter the product is isolated using ether. The ether solution is dried by means of magnesium sulphate, the ether is partially distilled off; the remaining portion of the solution is treated with ether saturated with hydrogen chloride, to yield 7.25 g (69.7% by weight) of 10'-Φβ-N-(1,4-diazabicyclo(4,3,0)-nonanyl)-propyonyl)-2'-trifluoromethylphenothiazine dichlorohydrate. M.p. 222°–223° C (in absolute alcohol).

Found: N 8.12%; S 6.23%; Cl' 13.38%; $C_{23}H_{26}N_3F_3Cl_2SO$.

Calculated: N 8.07; S 6.16; Cl' 13.62%.

EXAMPLE 2

The reaction is carried out in a manner similar to that described in Example 1, using the same starting reactants employed in equimolar ratio, upon heating in benzene for a period of 16 hours in the presence of triethylamine. The yield of 10'-(β-N-/1,4-diazabicyclo/4,3,0/-nonanyl/-propyonyl/-2'-trifluoromethylphenothiazine dichlorohydrate is 54% by weight.

EXAMPLE 3

Using a procedure similar to that of Example 1, from 6.48 g of 10-(β-chloropropyonyl)-2-chlorophenothiazine and 5.04 g of 1,4-diazabicyclo(4,3,0)-nonane 5.82 g (70% by weight) of 10'-(β-N-/1,4-diazabicyclo/4,3,0/-nonanyl/-propyonyl/-2'-chlorophenothiazine dichlorohydrate. M.p. 215°–216° C (in absolute alcohol). Found: N 8.75%; Cl 21.80%; Cl' 14.38%. $C_{22}H_{26}N_3Cl_3SO$. Calculated: N 8.63%; Cl 21.85%; Cl' 14.56%.

EXAMPLE 4

1 g of 10'-(β-N-/1,4-diazabicyclo/4,3,0/-nonanyl/-propyonly/)-2'-chlorophenothiazine dichlorohydrate is treated with a 40% aqueous caustic soda solution until the pH = 10; the resulting base is extracted with ether; the ether is evaporated; the residue is dissolved in 15 ml. of anhydrous methanol, whereafter 4.3 g. of methyl iodide are added and the mixture is boiled for 12 hours. Methanol is evaporated, the residue is crystallized from a mixture (1:4) of isopropanol and ethanol.

0.6 g (46% by weight) of 10'-(β-N-)1,4-diazabicyclo/4,3,0/-nonanyl/-propyonyl)-2'-chlorophenothiazine di-iodine methylate was obtained. M.p. 146°–148° C.

Found: J' 35.93%. $C_{23}H_{30}N_3ClJ_2SO$.
Calculated: J' 36.38.

EXAMPLE 5

To a solution of 2.9 g. of 10-(β-chloropropyonyl)-phenothiazine in 40 ml. of anhydrous toluene 2.52 g. of 1,4-diazabicyclo (4,3,0)-nonane are added. The mixture is boiled for 6 hours and treated in a manner similar to that described in Example 1 to yield 2.78 g. (61.5% by weight) of 10'-(β-N-/1,4-diazabicyclo/4,3,0/-nonanyl/-propyonyl)phenothiazine. M.p. 190.5°–191.5° C (in absolute alcohol).

Found: S 7.01%; N 9.01%; Cl' 15.35%; $C_{22}H_{27}N_3Cl_2SO$.

Calculated: S 7.09%; N 9.29%; Cl' 15.67%.

EXAMPLE 6

To a solution of 3.1 g of 10-chloracetyl-2-chlorophenethiazine in 40 ml. of anhydrous toluene 2.52 g. of 1,4-diazabicyclo(4,3,0)-nonane are added and the solution is boiled for 6 hours. The toluene solution is washed with water, acidified with a diluted solution of hydrochloric acid; the aqueous solution is treated with activated carbon, whereafter the carbon is filtered off and the filtrate is alkalized.

The product is extracted with ether, the ether solution is dried with magnesium sulphate and the ether is distilled off. 2.97 g. (74% by weight) of 10'-(N-/1,4-diazabicyclo-(4,3,0)-nonanyl/-acetyl)-2'-chlorophenothiazine are thus obtained. M.p. 132.5°–135.5° C.

Found: C 63.04%; H 5.57%; Cl 8.90%; N 10.35%. $C_{21}H_{22}N_3C_1SO$.

Calculated: C 63.05%; H 5.54%; Cl 8.865%; N 10.51%.

EXAMPLE 7

The reaction is carried out in a manner similar to that described in Example 6.2 g. of the resulting base 10'-(N-/1,4-diazabicyclo-(4,3,0)-nonanyl/-acetyl)-2'-chlorophenothiazine are dissolved in a small amount of absolute alcohol, whereafter ether saturated with hydrogen chloride is added thereto. 2 g (84% by weight) of 10'-(N-1,4-diazabicyclo/-4,3,0/-nonanyl/-acetyl)-2'-chlorophenothiazine dichlorohydrate are thus produced. M.p. 188°–189.5° C (in absolute alcohol-ether). Found: Cl' 1.467%. $C_{21}H_{24}N_3Cl_3SO$. Calculated: Cl 15.0%.

EXAMPLE 8

To a solution of 6.76 g of 10-( γ -chlorobutyroyl)-2-chlorophenothiazine in 50 ml. of anhydrous xylene 5.04 g of 1,4-diazabicyclo(4,3,0)-nonane are added and the mixture is boiled for 15 hours. The xylene solution is decanted the residue is washed with xylene, combined xylene solutions are washed with water, treated with a diluted solution of hydrochloric acid, the water layer is separated, boiled for 20 minutes with activated carbon, whereafter the carbon is filtered off; the filtrate is alkalized with a 40% caustic soda solution. The product is extracted with ether; the ether extract is dried with magnesium sulphate, the ether is partly filtered off, the residue is treated with ether saturated with hydrogen chloride. 5.04 g. (50.4% by weight) of 10'-( γ -N-/1,4-diazabicyclo-(4,3,0)-nonanyl/-butyroyl)-2'-chlorophenothiazine dichlorohydrate. M.p. 224-226° C (in absolute alcohol).

Found: Cl 21.03%; N 8.21%; $C_{23}H_{28}N_3Cl_3SO$.
Calculated: Cl 21.23%; N 8.38%.

EXAMPLE 9

The reaction is carried out in a manner similar to that described in Example 8. The starting products are employed in equimolar amounts and heated in anhydrous toluene in the present of a double excessive amount of anhydrous sodium carbonate and catalytical amount of potassium iodide for a period of 20 hours.

Then the mixture is filtered, the toluene solution is washed with water and further treated according to the procedure of Example 6.

The yield of 10'-( γ -N-/1,4-diazabicyclo(4,3,0)-nonanyl/-butyroyl)-2'-chlorophenothiazine dichlorohydrate is 43% by weight.

EXAMPLE 10

From 10-( β -chloropropyonyl)-2-trifluoromethylphenothiazine and 1,4-diazabicyclo(4,5,0)-undecane using a procedure similar to that described in Example 1, 10'-( β -N-/1,4-diazabicyclo(4,5,0)-undecanyl/-propyonyl)-2'-trifluoromethyl-phenothiazine dichlorohydrate is produced. The yield is 64% by weight. The resulting product is a hydrate having one water molecule and possessing no distinct melting temperature.

Found: H$_2$O 3.5%; Cl' 12.45%; N 7.25%; S 5.68%. C$_{25}$H$_{30}$N$_3$F$_3$Cl$_2$SO.H$_2$O. Calculated: Cl' 12.51%; N 7.42%; S 5.66%.

EXAMPLE 11

To the alcoholic solution of 3.4 g of 10' [β-N/1,4 diazabicyclo [4,3,0] nonanyl) propyonyl]-2'-chlorophenothiazine produced by following the procedure described in Example 3 there is added a solution of 1.3 g of tartaric acid in absolute alcohol. 2.7 g/60 wt.%) of 10'- [β -N- (1,4-diazabicyclo [4,3,0] nonanyl) propyonyl]-2'-chlorophenothiazine tartrate are produced.

Found: C 53.61%; H 5.74%; N 6.73% C$_{26}$H$_{30}$N$_3$ClSO$_7$.H$_2$O. Calculated: C 53.65%; H 5.54%; N 7.21%

EXAMPLE 12

To the ether solution of 3.4 g of the base of 10'-[β-N-(1,4-diazabicyclo [4,3,0] -nonanyl) propyonyl] -2'-chlorophenethiazine produced by following the procedure described in Example 3 there is added a solution of 1.9 g of fumaric acid in 40 ml of absolute alcohol the solvent is evaporated dry, the residue is dried, and 4.9 g (94 at %) of 10'-[β-N-(1,4-diazabicyclo [4,3,0] nonanyl) propyonyl]-2'-chlorophenothiazine difumarate are produced. M.p. 157°–159° C.

Found: C 55.78%; H 5.32%; N 6.21%. C$_{30}$H$_{32}$N$_3$ClSO$_9$. Calculated: C 55.77%; H 4.99%; N 6.50.

EXAMPLE 13

To an ether solution of 45 g of the base of 10'-[β -N-(1,4-diazabicyclo [4,3,0] nonanyl)-propyonyl]-2'-chlorophenothiazine produced by following the procedure described in Example 3, there is added a solution of 2.5 g of maleic acid in 30 ml of absolute alcohol. 5.1 g (72.8 at %) of 10'-[β -N-(1,4-diazabicyclo [4,3,0] nonanyl)-propyonyl]-2'-chlorophenothiazine diamaleate are produced. Found: C 55.60%; H 4.99%; N 6.71%. C$_{30}$H$_{32}$N$_3$ClSO$_9$. Calculated: C 55.77%; H 4.99%; N 6.50%.

EXAMPLE 14

To an alcoholic solution of 2.7 g of the base of 10'-[β -N-(1,4-diazabicyclo [4,3,0] nonanyl)-propyonyl]-2'-chlorophenothiazine produced by following the procedure described in Example 3 there is added a solution of 1.2 g of 94% sulphuric acid in absolute alcohol. 3 g (81 wt.%) of 10'-[β -N-(1,4-diazabicyclo [4,3,0] -nonanyl)-propyonyl]-2'-chlorophenothiazine disulphate are produced.

Found: C 43.25; H 5.04; S 15.50; N 6.85; C$_{22}$H$_{24}$N$_3$ClSO.2H$_2$SO$_4$. Calculated: C 43.31; H 4.63; S 15.76; N 6.89.

We claim:

1. A pharmaceutical composition possessing a spasmolytic and coronary-dilatant effect containing, as the active ingredient, a spasmolytic and coronary-dilatant amount of 10'-[β-N-(1,4-diazabicyclo (4,3,0)-nonanyl)-propionyl]-2'-chlorophenothiazine in a pharmaceutical carrier.

2. A pharmaceutical composition as claimed in claim 1, containing said active ingredient in combination with a pharmaceutical filler for tablets.

3. A pharmaceutical composition as claimed in claim 2, wherein said pharmaceutical filler for tablets is selected from the group consisting of starch and powdered sugar.

4. A pharmaceutical composition as claimed in claim 1, in unit dosage form containing the active ingredient in an amount of 15–90 mg.

* * * * *